United States Patent [19]

Whiteley et al.

[11] Patent Number: 4,617,264
[45] Date of Patent: Oct. 14, 1986

[54] PRETREATMENT METHOD AND COMPOSITION

[75] Inventors: Gordon R. Whiteley, Palo Alto; Cynthia G. Pritchard, Mountain View; Sharon S. Barrett, East Palo Alto, all of Calif.

[73] Assignee: Syntex (U.S.A.) Inc., Palo Alto, Calif.

[21] Appl. No.: 549,522

[22] Filed: Nov. 4, 1983

[51] Int. Cl.[4] .............................................. C12Q 1/04
[52] U.S. Cl. ........................................ 435/34; 435/7; 435/18; 435/29; 435/38; 435/871; 436/533; 436/534; 436/548; 436/511
[58] Field of Search ................... 435/18, 34, 38, 7, 29, 435/871; 436/533, 534, 548, 800, 509, 511

[56] References Cited

U.S. PATENT DOCUMENTS

| | | | |
|---|---|---|---|
| 3,088,875 | 5/1963 | Fisk | 436/509 |
| 3,880,715 | 4/1975 | Schneider | 435/7 |
| 4,281,061 | 7/1981 | Zuk et al. | 436/800 |
| 4,443,549 | 4/1984 | Sadowski | 436/548 |

OTHER PUBLICATIONS

Audiffren et al., C. R. Societe De Biologie, (1967), vol. 161, No. 6, pp. 394–396.
Arko et al., Journal of Clinical Microbiology, (1979), vol. 9, No. 4, pp. 517–519.
Chemical Abstracts, Item No. 106197t, vol. 67, 1967, p. 9997.
Caldwell et al., (1984), Infection and Immunity, vol. 44, No. 2, pp. 306–314.
Repaske, Biochimica et Biophysica Acta (1958), vol. 39, pp. 225–232.

*Primary Examiner*—Sidney Marantz
*Assistant Examiner*—William J. Herald
*Attorney, Agent, or Firm*—Theodore J. Leitereg; Carole F. Barrett

[57] ABSTRACT

The method disclosed herein allows for the pretreatment of organisms, suspected of being a material of interest, prior to performing an assay for a determination thereof. The method comprises contacting the organism in an aqueous medium with a composition comprising (1) an enzyme capable of hydrolyzing bonds between N-acetylglucosamine and N-acetylmuramic acid and (2) a chelating agent, in amounts and under conditions sufficient to produce a homogeneous suspension of the organism of interest in the aqueous medium but insufficient to produce lysed cells or spheroplasts. The method and composition are particularly applicable to the pretreatment of cells of gram negative bacteria such as, for example, *N. gonorrhoeae*, and of chlamydia.

22 Claims, No Drawings

PRETREATMENT METHOD AND COMPOSITION

BACKGROUND OF THE INVENTION

1. Field of the Invention

This invention is related to and has among it objects the provision of improved assay methods for detection of organisms. Primarily, the present invention is directed to assay methods involving immuno-reactions such as, for example, agglutination assays, enzyme immunoassays, and the like.

Agglutination assays have been used to detect the presence of an organism in a specimen, the assays finding extensive use in serological testing, typing of organisms, and bacterial culture confirmation. A variety of agglutination protocols have been used. In direct agglutination assays an antigen is present on the surface of a cell. Addition of an antibody specific for the antigen causes the cells to bind together through antigen antibody complexing thus producing a precipitate (agglutinate). The formation of an agglutinate indicates a positive test in the agglutination assay.

In a variation of the above method antigen is absorbed onto or linked to a cell. Addition of antibody causes the cells containing the absorbed antigen to agglutinate.

In reverse passive agglutination antibody is linked or absorbed onto the surface of a cell or latex particle. When antigen is present in the test medium, the cells or particles having antibody on their surface will agglutinate. Other variations of agglutination assays are known in the art.

Another assay involving an immuno-reaction is the enzyme-linked immunoadsorbent assay (ELISA), which has found considerable popularity for detecting and quantitating an organism. In the ELISA, an antigen or antibody is labeled with an enzyme. The labeled member is combined with the organism after which the enzyme-labeled antigen-antibody complex is separated from free enzyme-labeled antigen or antibody. The enzymatic activity in the bound or free fraction is quantitated by the enzyme-catalyzed conversion of a relatively nonchromatic or non-fluorescent substrate to a highly chromatic or fluorescent product.

For assays involving antigens, such as bacterial antigens of intact bacteria, a pretreatment step of the bacterial culture is often required. The pretreatment step is necessary to provide a homogeneous suspension of the test antigens in the test medium and to expose antigens of interest for access to the reaction. Without the application of a pretreatment step clumps and strands of organisms are present in the test medium giving rise to uninterpretable control reactions. The coagulation lattice tends to adhere to these clumps and strands, making differentiation between the test and the control reactions difficult.

Various pretreatment methods for organisms which are to be subjected to an assay are known. For example, organisms to be tested may be boiled for at least five minutes prior to the testing. The boiling procedure is, however, time consuming and laborious. The boiling step is not easily controlled and destroys some proteins (denaturation) indiscriminately which may reduce the density of certain epitopes or denature them so that they are no longer able to react with specific antibody. Enzymatic pretreatment steps are also known, with proteases and nucleases having been employed.

2. Description of the Prior Art

The bacterial cell is discussed in "Bacterial Morphology and Ultrastructure," Joklik et al (eds.). Zinsser Microbiology, pages 28–47, Appleton-Century-Crofts, New York, New York (1976). Various pretreatments for optimal performance of an agglutination test are disclosed in the following: Anand et al., *J. Clinical Micro.*, 12:15–17 (1980); Lue et al, *J. Clin. Micro.* 8:326–328 (1978); Stockman et al, *J. Clin. Micro.*, 16:965–967 (1982); Arko et al, *J. Clin. Micro.* 9:517–519 (1979). Lysis of gram negative organisms and the role of ethylenediaminetetraacetic acid in such lysis is discussed by Repaske, *Biochimica et Biophysicia Acta,* 30:225–232 (1958). Improved techniques for the preparation of bacterial lipopolysaccharides is discussed by Johnson et al, *Can. J. Microbiol.*, 22:29–34 (1976).

SUMMARY OF THE INVENTION

The method disclosed herein is an improved assay method which allows for the pretreatment of organisms, prior to performing an assay for a determination thereof. The pretreatment comprises contacting the organism in an aqueous medium with a composition comprising (1) an enzyme capable of hydrolyzing bonds between N-acetylglucosamine and N-acetylmuramic acid and (2) a chelating agent, in amounts and under conditions sufficient to produce a homogeneous suspension of the organism of interest in the aqueous medium but insufficient to produce lysis of the cells of the organism. The method and composition are particularly applicable to the pretreatment of cells of gram negative bacteria such as, for example, *N. gonorrhoeae*.

DESCRIPTION OF THE SPECIFIC EMBODIMENTS

As mentioned above the present method provides for pretreatment of organisms, such as bacteria, viruses, chlamydia, etc., prior to performing an assay for the determination thereof. The organisms are contacted in an aqueous medium with a composition comprising (1) an enzyme capable of hydrolyzing bonds between N-acetylglucosamine and N-acetylmuramic acid (NAG-NAMA bonds) and (2) a chelating agent. The amounts of the above reagents and the conditions under which the organism sample is treated are sufficient to produce a homogeneous suspension of the material of interest in the aqueous medium but insufficient to result in lysed cells or spheroplasts. By the term "homogeneous suspension" is meant that cells treated in accordance with the invention will not clump or form strands or fibers to any substantial degree such that the clumps or strands or fibers would cause interference in an assay.

As the enzyme one may use any enzyme capable of hydrolyzing a NAG-NAMA bond. The preferred enzyme will be lysozyme.

The chelating agent should be one which is capable of chelating magnesium for example, carboxyalkyl polyaminoalkylenes wherein the alkyl contains from 1–3 carbon atoms, the alkylenes contain from 2 to 4 carbon atoms, and the amino groups are 1,2-disubstituted on the alkylene, and wnerein from 1 to 4 carboxyalkyl groups are substituted on the alkylene, such as ethylenediaminetetraacetic acid (EDTA), and salts thereof.

The enzyme will generally be employed in the composition in an amount such that an aqueous solution thereof would contain from about 10 to 150 micrograms per milliliter, preferably 50 to 100 micrograms per milliliter, for an enzyme having a specific activity of about 15,000-30,000 units/mg, preferably about 20,000 units/mg and for a concentration of organism of from about $10^6$ to $10^8$ colony forming units (cfu) per milliliter of solution. The particular amount of the enzyme employed, of course, will depend on the specific activity of the enzyme preparation. Thus, where the specific activity of the enzyme would be greater than the above, less of the enzyme would be used; and, where the specific activity of the enzyme is less than the above more of the enzyme will necessarily be used. The appropriate amounts of the enzyme to be used can be determined by pilot trials in accordance with the foregoing discussion.

The chelating agent will be present in the composition in an amount such that an aqueous solution would contain from about 0.5 to 5 micromoles per ml for an organism concentration of from about $10^6$ to $10^8$ cfu per milliliter of solution.

The amounts of the above reagents employed could, of course, vary with the sample size. The particular amounts referred to above pertain to a sample which would be about one milliliter. Thus, the amounts of the above reagents to be used for a sample size outside of the above range can be determined readily following the above guideline. In addition, the amounts of the above reagents can vary depending on the nature of the organism and the nature of the assay for the determination of the organism. Again the appropriate amounts of the reagents can be determined by pilot trials following the teaching herein.

The controlling factor in the determination of the maximum concentration of the enzyme and the chelating agent is that the formation of lysed cells and spheroplasts be substantially avoided. We have found that ennanced sensitivity is obtained in an assay method when the organism to be determined is pretreated in accordance with our method without formation of lysed cells or spheroplasts.

The pH of the aqueous medium should be in the range of about 7 to 10 depending upon the stability of the reagents employed. Preferably the pH should be in the range of about 7.5 to 8.5.

As customary in the art, the aqueous medium may contain a small amount of a salt such as sodium chloride, potassium chloride, calcium chloride, and the like. Generally, for optimum results the salt concentration of the aqueous medium is generally within the range of about 40 mM to 160 mM.

The temperature at which the pretreatment is conducted should be from about 15°-30° C., preferably about 20° to 25° C. and the period of pretreatment should be from about 0.5 to 10 minutes, preferably, 1-5 minutes.

In general, the type of assay in which the pretreatment method and composition of the present invention find particular use are those assays in which an immunoreaction is involved. Thus, the assay is dependent upon binding, either competitively or non-competitively, between members of a specific binding pair, normally ligand and its homologous receptor. Ligand is any material for which there is a reciprocal binding member; therefore ligands will be haptens and antigens. Receptors will be compounds which recognize a particular spatial and polar conformation of the ligand.

The pretreatment method of the invention is applicable to the treatment of gram negative bacteria and to other organisms which have a lipopolysaccharide layer such as, for example, chlamydia. The method of the invention finds use, for example, in the pretreatment of *N. gonorrhoeae* particularly for an agglutination assay for detecting the presence of *N. gonorrhoeae* or in the pretreatment of chlamydia particularly for an ELISA for detecting the presence of chlamydia.

Next there will be described in general terms the nature of the pretreatment method of the invention. The present method may be applied directly to a specimen from a patient or the organism may first be separated from the specimen. In the latter approach, a portion of the specimen may be taken and subjected to incubation under conditions known to propagate the organism to produce a clinical isolate. This usually involves taking a portion of the material of interest, combining it with a culturing medium, and holding the combination for a period of time and at a temperature to culture cells of the organism. Illustratively, for the organism *N. gonorrhoeae* a specimen is secured and a portion of the specimen is combined with a differential medium and then held for a period of about 24 to 48 hours at a temperature of about 35° to 37° C.

The specimen from the patient, or the clinical isolate as the case may be, is then mixed with the pretreatment composition, prepared as described above, in an aqueous medium in order to produce a homogeneous suspension of the cells in the aqueous medium. The suspension is now ready for application of an assay method to determine the material of interest.

In an agglutination assay the homogeneous suspension of the cell suspected of being the organism is mixed with a substance capable of agglutinating in the presence of the organism. Generally, the substance is capable of specific binding with the organism. For the most part, the substance capable of agglutinating in the presence of the organism will be a receptor specific for the material of interest. Preferably, the substances will be antibody specific for the organism and more preferably a monoclonal of antibody specific for the material of interest. For example, in the situation where the presence of *N. gonorrhoeae* is suspected. The substance capable of agglutinating in the presence of *N. gonorrhoeae* will be a monoclonal antibody which is specific for *N. gonorrhoeae*.

In the agglutination assay, carrier particles are then coated with the substance capable of agglutinating in the presence of the organism. These carrier particles may be polystyrene latex microspheres such as those described, e.g., in U.S. Pat. No. 3,088,875. However, other passive carriers may also be employed such as, for example arylic acid derivatives (Manecke et al., *Pure Appl. Chem.*, 1962 4, 507), acrylamides derivatives (Inman et al., *Biochem*, 1969, 8, 4074), red blood cells, and Staphylococcus aureus. See also Silman et al., *Ann. Rev. Biochem.*, 1966, 35, 873.

The type of agglutination which has been described above is referred to as passive or indirect agglutination which refers to the agglutination of coated cells or particles which are passive carriers of otherwise soluble components. These types of agglutinations are well documented as illustrated in U.S. Pat. Nos. 4,310,508, 3,171,783, 3,775,536, 3,873,683, 3,879,262, 4,003,988, and 4,054,384.

The mixture from above is then incubated, which generally involves holding the mixture at a temperature of about 15°-30° C., preferably about 20° to 25° C., usually at ambient temperature, for a period of about 0.5 to 5 minutes to allow the agglutination to occur. The presence of an agglutinate is an indication of the presence of the material of interest in the specimen.

In an ELISA, the homogeneous suspension of the cells suspected of being the organism of interest (e.g., chlamydia) is mixed with a receptor, specific for the material of interest, labeled with an enzyme. The mixture is incubated. The enzyme labeled complex of the material of interest and its receptor is separated from the free enzyme labeled receptor and the enzymatic activity of one of the separated fractions is determined and will be related to the presence or absence of the organism in the sample or specimen.

The primary advantage of the present invention is that a homogeneous suspension of the test cells or organisms is provided. The pretreated cells when used in an assay provide for an enhanced signal, i.e., for example, the production of more agglutinate in an agglutination assay, which increases the accuracy of the assay. The pretreated cells do not clump or form strands thus avoiding false positive tests in agglutination assays and allowing for differentiation between positive tests and controls.

Another advantage of the present invention is that it is easy to perform and requires only a short amount of time. Furthermore, the pretreatment step is easily controlled. The composition of the invention in the appropriate amounts is specifically directed to the particular sites on the organism that affect the optimal performance of an assay.

EXAMPLES

The invention is further demonstrated by the following illustrative examples: All percents and parts not otherwise indicated are by weight, except for mixtures of liquids which are by volume. All temperatures not otherwise indicated are centigrade. The following abbreviations are employed:

EDTA—ethylenediaminetetraacetic acid;
RPM—rotations per minute; and
GBS—glycine buffered saline containing 0.1 M glycine, 0.15 M sodium chloride, pH 8.2.

Presumptive *N. gonorrhoeae* colonies (oxidase positive, catalase positive, gram negative diplococci from blood, chocolate or Thayer-Martin agar or other selective media for *N. gonorrhoeae*) were picked from a plate and placed into 0.5 ml of GBS containing 0.5 mM EDTA and 10 µg/ml of lysozyme (specific activity 20,000 units/mg). The mixture was held for 1 minute at room temperature to give a homogeneous suspension of the cells in the aqueous medium.

Thirty µl of the above suspension was mixed with an equal amount of antibody sensitized beads prepared as follows: Polystyrene latex beads (0.8 micrometers, carboxylated were obtained from Polysciences, Inc., Warrington, PA, and were further treated in accordance with the disclosure of Ito et al., *J. Clin. Microbiology* 17, 7-12 (1983).

Monoclonal antibodies specific for *N. gonorrhoeae*, prepared in the customary fashion, were absorbed onto the beads, usually 500 µg of monoclonal antibody per 10 mg of beads. The monoclonal antibody was added to the bead suspension, and the mixture was incubated for 12 hours at 37° C. with slow, constant shaking to keep the beads dispersed.

The beads were pelleted by centrifugation of the suspension as described above. The bead pellets were washed with 10 ml of glycine buffered saline to remove weakly absorbed monoclonal antibody. The beads were then pelleted as described above and washed as described above.

The beads were suspended together with absorbed antibody in 10 ml of glycine buffered saline and 2 mg/ml of bovine serum albumin was added. The bovine serum albumin was allowed to cover the unblocked portions of the beads by incubating the suspension for 2 hours at 37° with slow, constant shaking.

The beads were pelleted by centrifigation as described above and washed as before. The final bead pellets were suspended in glycine buffered saline with 0.1% sodium azide at a final concentration of 2 mg/ml beads. The preparation was stored at 4°. Thirty microliters of the suspension of the *Neisseria gonorrhoeae* cells was mixed on a slide with thirty microliters of the above aqueous suspension containing antibody sensitized beads. The slide was then rotated for one minute. A positive test result was indicated by a strong, even clumping of the latex particles.

The above described pretreatment abrogates autoagglutination of the organism of interest in the test thereby eliminating false positive reactions. It has the added advantage of increasing the signal in the assay over that observed with other pretreatments such as, for example, boiling or nuclease pretreatments. Consequently, the results of the test are much more easily read. The pretreatment of the invention has no requirement for any special apparatus and everything needed to perform the assay can be included in a test kit.

A test kit for use in conjunction with the present invention would comprise, in a packaged combination, a pretreatment composition as described above containing the enzyme and the chelating agent in the appropriate amounts. A second composition would be included which would be a receptor for the organism of interest such as an antibody for the organism. Other ancillary materials such as buffers and the like would be included.

What is claimed is:

1. A method for pretreating an organism suspected of being a material of interest in a specimen prior to performing an assay for a determination thereof, which comprises contacting a speciment suspected of containing an organism in an aqueous medium with a composition comprising (a) an enzyme capable of hydrolyzing bonds between N-acetylglucosamine an N-acetylmuramic acid and (b) a chelating agent for magnesium, in an amount and under conditions sufficient to produce a homogeneous suspension of the organism in the aqueous medium but insufficient to produce lysed cells or spheroplasts.

2. The method of claim 1 wherein the specimen is biological tissue.

3. The method of claim 1 wherein the organism is a gram negative bacteria.

4. The method of claim 1 wherein the organism is *Neisseria gonorrhoeae*.

5. The method of claim 1 wherein the enzyme is lysozyme.

6. The method of claim 1 wherein the chelating agent is a carboxyalkyl polyaminoalkylene or a salt thereof wherein the alkyl contains from 1 to 3 carbon atoms, alkylene group has from 2 to 4 carbon atoms, the amino groups are 1, 2 disubstituted on the alkylene, and from 1 to 4 carboxyalkyl groups are substituted on the alkylene.

7. The method of claim 1 wherein the enzyme is present in the aqueous medium in an amount of from about 10 to 150 micrograms of enzyme of specific activity of about 15,000–30,000 units/mg per milliliter of the aqueous medium containing from about $10^6$ to $10^8$ colony forming units of the organism per milliliter of the aqueous medium.

8. The method of claim 1 wherein the chelating agent is present in the aqueous medium in an amount of from about 0.5 to 5 micromoles per milliliter of the aqueous medium containing from about $10^6$ to $10^8$ colony forming units of the organism.

9. The method of claim 1 wherein the aqueous medium has a pH of from about 7 to 10.

10. The method of claim 1 wherein pretreatment is conducted at a temperature of from about 15° to 30° C. for a period of from about 0.5 to 10 minutes.

11. A method for pretreating an organism suspected of being a material of interest in a specimen prior to performing an assay for a determination thereof, which comprises contacting a specimen suspected of containing an organism in an aqueous medium with a composition comprising (a) an enzyme capable of hydrolyzing bonds between N-acetylglucosamine and N-actylmuramic acid and (b) ethylenediametetraacetic acid or a salt thereof in an amount and under conditions sufficient to produce a homogeneous suspension of the organism in the aqueous medium but insufficient to produce lysed cells or spheroplasts.

12. A method for determining the presence of an organism of interest in a specimen suspected of containing the same, which comprises
   (a) contacting a specimen with a composition for pretreatment of a specimen suspected of containing an organism of interest to produce a homogeneous suspension of the organism in an aqueous medium, which comprises lysozyme and ethylenediaminetetraacetic acid or a salt thereof in amounts such that an aqueous medium thereof would contain about 10 to 150 micrograms per milliliter of lysozyme of specific activity of about 15,000–30,000 units/mg and about 0.5 to 5 micromoles per milliliter of ethylenediaminetetraacetic acid or a salt thereof per $10^6$ to $10^8$ colony forming units of organism per milliliter of the medium, wherein said amounts and conditions are sufficient to produce a homogeneous suspension of the organism in the aqueous medium but insufficient to produce lysed cells or spheroplasts; and
   (b) subjecting the speciment to an assay involving an immuno-reaction to determine the presence of said organism.

13. The method of claim 12 wherein cells of an organism of interest are separated from the specimen prior to contact with said composition.

14. The method of claim 12 wherein said method comprises determining the presence of an agglutinate and wherein the specimen in step b is subjected to
   (a) mixing with a substance capable of agglutinating in the presence of the organism of interest to which is bound a material capable of binding with the organism of interest
   (b) incubating the mixture, and
   (c) determining the presence of an agglutinate, the presence of an agglutinate indicating the presence of the organism of interest in the specimen.

15. The method of claim 14 wherein the substance capable of agglutinating in the presence of the organism of interest is a polystyrene latex bead coated with antibody specific for the organism of interest.

16. The method of claim 15 wherein the latex beads are coated with monoclonal antibody specific for the organism of interest.

17. The method of claim 12 wherein the specimen in step (b) is subjected to
   (a) mixing with a receptor which is specific for the organism and which is labeled with an enzyme,
   (b) incubating the mixture,
   (c) separating a complex of said organism and said receptor from said mixture, and
   (d) determining the enzyme activity of said complex or said mixture wherein the enzyme activity is related to the presence or absence of said organism of interest in the sample.

18. A kit for use in an agglutination assay to detect the presence of an organism of interest in a specimen sample suspected of containing the same, whic comprises in a packaged combination in predetermined ratios for combination with said sample
   (a) a first composition comprising lysozyme and etylenediaminetetraacetic acid or a salt thereof in amounts such that an aqueous solution thereof would contain from about 10 to 150 micrograms per milliliter of lysozyme of specific activity of about 15,000–30,000 units/mg and from about 0.5 to 5 micromoles per milliliter of ethylenediaminetetraacetic acid, per $10^6$ to $10^8$ colony forming units or organism per milliliter of said aqueous solution, and wherein the amounts and conditions are sufficient to produce a homogneeous suspension of the organism in the homogeneous suspension of the organism in the aqueous medium but insufficient to product lysed cells or spheroplasts,
   (b) a second composition comprising a substance capable of agglutinating in the presence of an organism of interest to which is bound a material capable of binding with the organism of interest, and
   (c) ancillary agents as necessary for conducting the agglutination assay.

19. The kit of claim 18 wherein the substance is a polystyrene latex bead which is coated with monoclonal antibody specific for the material of interest.

20. In an assay method for the detection of an organism of interest, the improvement which comprises contacting a sample suspected of containing said organism of interest, prior to conducting said assay method, with a composition comprising lysozyme and ethylenediaminetetraacetic acid or a salt thereof in an amount and under conditions sufficient to produce a homogeneous suspension of said organism in an aqueous medium but insufficient to produce lysed cells or spheroplasts.

21. In an agglutination assay for the detection of cells of a gram negative bacteria which may be present in a specimen, which assay comprises (a) combining the specimen in an aqueous medium with a particle capable of agglutinating in the presence of cells of the gram negative bacteria, (b) incubating the mixture, and (c) determining the presence of agglutination, the presence of agglutination indicating the presence of the gram negative bacteria in the specimen, the improvement which comprises contacting the specimen prior to mixing with the particle, with a composition comprising an enzyme capable of hydrolyzing N-acetylglucosamine-N-acetylmuramic acid bonds and a chelating agent capable of chelating magnesium in amounts and under conditions sufficient to produce a homogeneous suspension of the cells in the aqueous medium but insufficient to produce lysed cells or spheroplasts.

22. The assay of claim 23 wherein a portion of the specimen is cultured under conditions sufficient to result in a growth of the number of cells of the gram negative bacteria and said portion is combined with said particle in step (a).

* * * * *